_United States Patent_ [19]

Queuille et al.

[11] 4,007,264
[45] Feb. 8, 1977

[54] METHOD OF TREATING DIARRHEA EMPLOYING A FORMALDEHYDE-MODIFIED CASEIN

[75] Inventors: Andre Queuille, Noisy-le-Sec; Raymond Larde, Coubron, both of France

[73] Assignee: Roussel-UCLAF, Paris, France

[22] Filed: Jan. 30, 1975

[21] Appl. No.: 545,160

Related U.S. Application Data

[63] Continuation of Ser. No. 870,356, Sept. 30, 1969, abandoned.

[30] Foreign Application Priority Data

Oct. 7, 1968   France ............................ 68.168987

[52] U.S. Cl. .................................................. 424/82
[51] Int. Cl.$^2$ ........................................ A61K 31/74
[58] Field of Search ............... 260/6; 424/82, 79

[56] References Cited

UNITED STATES PATENTS

| | | | |
|---|---|---|---|
| 1,542,006 | 6/1925 | Sauer | 424/125 |
| 1,589,081 | 6/1926 | Adler | 424/125 |
| 1,949,266 | 2/1934 | Bird | 424/154 |
| 2,110,208 | 3/1938 | Eggert | 424/177 |
| 2,139,139 | 12/1938 | Tompkins | 424/180 |
| 2,828,242 | 3/1958 | Bennett | 424/154 |
| 2,918,405 | 12/1959 | Barr et al. | 424/155 |
| 3,041,238 | 6/1962 | Allegrini | 424/154 |
| 3,164,518 | 1/1965 | Mussill et al. | 424/125 |
| 3,297,664 | 1/1967 | Miskel et al. | 424/79 |
| 3,699,219 | 10/1972 | Carlson | 424/14 |
| 3,725,541 | 4/1973 | Queuille et al. | 424/80 |

FOREIGN PATENTS OR APPLICATIONS 1,467,792   12/1968   Germany
242,335      5/1946   Switzerland

OTHER PUBLICATIONS

Brother et al, _I&EC_, vol. 30, No. 11, pp. 1236–1240, Nov. 1938.
Craig et al, _Ann. N. Y. Acad. Sci._, vol. 57, pp. 67–78, 1953.
Neissner, _Pharm. Ind._, 1968, vol. 30, pp. 425–429.
Translation of Awg et al, Pharm. Ind. 21:368–370 (1959) "Experience in Tabletting the New Disintegrant Formaldehyde–Casein".
C.A. No. 2478 (1921), 43 No. 7787c (1949); 45 No. 9664e (1951); 54 No. 19890b (1960).
C.A. 55 No. 2017b (1961).
Manier, Seminars in Drug Treatment 3(4):321–329 Spring 1974, "Diarrhea and Constipation: Mechanism and Treatment".
C.A. 64 No. 6411g (1966).
Martin, "Ion Exchange and Adsorption Agents in Medicine, The Concept of Intestinal Bionomics" 1955, pp. 228–245, Little Brown & Co., Boston, Mass.

_Primary Examiner_—Shep K. Rose
_Attorney, Agent, or Firm_—Hammond & Littell

[57] ABSTRACT

The method of treating chronic or infectious diarrhea by oral administration of an effective amount of a formaldehyde-modified casein; as well as pharmaceutical compositions.

2 Claims, No Drawings

METHOD OF TREATING DIARRHEA EMPLOYING A FORMALDEHYDE-MODIFIED CASEIN

REFERENCE TO A PRIOR APPLICATION

This application is a continuation of Ser. No. 870,356, filed Sept. 30, 1969, and now abandoned.

THE PRIOR ART

The obtention of formaldehyde-modified casein by the action of formaldehyde on casein is known, see, for example, J. F. Walker, Formaldehyde, 3rd Edition Reinhold, (1964) pages 399,402, and Allmanns Encyklopadie der Technischen Chemie 14 (1963), page 431. These formaldehyde-modified caseins have been used as plastic resins.

OBJECTS OF THE INVENTION

It is an object of the invention to provide novel pharmaceutical compositions containing a formaldehyde-modified casein as the active ingredient.

It is another object of the invention to provide a novel method of treating intestinal diseases, particularly diarrhea in humans and warm-blooded animals.

It is a further object of the invention to provide a novel method of treating cutaneous diseases caused by toxins.

These and other objects and advantages of the invention will become obvious from the following detailed description.

THE INVENTION

The therapeutic compositions of the invention are comprised of an effective amount of a formaldehyde-modified casein and a major amount of a pharmaceutical carrier. These compositions may also contain other active ingredients such as antibiotics, for example framycetin sulfate, kanamycin sulfate, gentamycine sulfate, neomycin sulfate, etc., or intestinal antiseptics, for example 5-chloro-7-iodo-8-oxyquinoline, benzonaphtol, sulfanilamidothiazole-formaldehyde, hexamethylene tetramine, or vitamins, i.e. pyridoxin, biotin or pyridoxal.

The therapeutic compositions of the invention have interesting pharmacological properties. They are useful in the treatment of intestinal diseases, more particularly in the treatment of chronic or infectious diarrhea. They may be used for the treatment of infectious or chronic diarrhea caused by infections, food poisonings, changes in diet, excessive use of laxatives, or by diseases of extra-intestinal origin, in particular, diarrhea and diseases of digestion following treatment with antibiotics. They do not give rise to secondary effects, such as constipation, which is frequently observed with many antidiarrhea products. Moreover, they are practically non-toxic.

Said therapeutic compositions are administered orally. They may be in the form of tablets, capsules, aromatized powder, suspensions, sachets and aromatized granules. These pharmaceutical forms are prepared according to usual methods.

The method of the invention for treating intestinal diseases, e.g. diarrhea, in warm-blooded animals comprises orally administering to humans or warm-blooded animals an effective amount of a formaldehyde-modified casein.

The effective amount of formaldehyde-modified casein is defined below by the daily dosage and is exemplified in the experimental part of the description. The useful daily dosage is between 25 and 125 mg/kg of active material for oral administration. In the adult, the daily dosage is 2 to 10 gm of active product, generally by one or several administrations of from 1 to 4 gm of active product at each time.

The therapeutic compositions of the invention are also useful for the treatment of cutaneous diseases caused by the action of internal or external toxins. In that case, the compositions of the invention are used topically. They are then prepared in the form of creams, pommades, jellies, tooth paste and dry dressings which are prepared according to usual methods.

The method of the invention for treating cutaneous diseases caused by toxins comprises topically applying an effective amount of a formaldehyde-modified casein.

The formaldehyde-modified caseins used in the compositions and methods of the invention are prepared according to known methods, by the action of formaldehyde on a casein, for example rennet casein.

It is known that formaldehyde-modified proteins, particularly caseins, are principally composed of protein chains and micellar units cross-linked by methylene bonds connecting the reactive groups; J.F. Walker, Formaldehyde, Reinhold, 3rd Edition (1964) pages 399,402. As this author indicates "casein fixes a maximum of only 0.6 to 2.5 grams per 100 grams". The action of formaldehyde on casein results in blocking amino, imino and phenolic groups of casein. When the reaction is performed in an aqueous medium, the polypeptide chain is also hydrated. The formaldehyde-modified caseins are also sometimes called "formo caseins" or "methylenic caseins".

The polymers thus obtained are insoluble in water. However, they swell in water by capillarity effect.

The formaldehyde-modified caseins are also commercially available. One of the presently preferred formaldehyde-modified caseins for the compositions and methods of the invention, is sold in France by S.P.C.I. Company under the trade name of "Capillact". It consists of a formaldehyde-modified casein which occurs in the form of a white-yellowish powder, whose granules are less than 0.250 mm in size, insoluble in ethyl ether, benzene, dilute acids, ethanol and water, which may retain important amounts of water by capillarity. The commercial product contains about from 7 to 8 % of water and about 2 % of formaldehyde. The formaldehyde-modified caseins used in the compositions and methods of the invention are free of unreacted formaldehyde.

In the following examples, there are described several preferred embodiments to illustrate the invention. However, it should be understood that the invention is not intended to be limited to these specific embodiments.

EXAMPLE 1

Preparation of a formaldehyde-modified casein 50 kgm of rennet casein were introduced into a pebble-mill. 0.500 liters of a 40% formaldehyde solution were added and the pebble-mill was rotated for twenty minutes. Another 0.500 liters of the 40% formaldehyde solution were added thereto and the pebble-mill as rotated again for twenty minutes, and so on until a total introduction of 2 liters of the formaldehyde solution. After the last introduction of formaldehyde, the pebble-mill was rotated for four hours. The pasty product thus obtained was washed with water till complete elimination of formol, laid on drying hurdles and dried in a drying oven with air circulation. The formaldehyde-modified casein thus obtained occurred in the form of a powder, insoluble in water.

EXAMPLE 2

Aromatized granules in sachet units

|  | Grams |
|---|---|
| "Capillact" | 2 |
| Citric acid | 0.10 |
| "Pluronic F 68" | 0.015 |
| Sodium cyclohexylsulfamate | 0.012 |
| Sodium saccharinate | 0.006 |
| Solid flavors } Liquid flavors } | 0.07 |
| Sugar powder, in a sufficient quantity for obtaining a total weight of 10 gm. | |

"Capillact", citric acid, "Pluronic F 68", synthetic sweeteners, the solid flavors and sugar were admixed in a dry state. The liquid flavors were dissolved in an 80% ethanol solution, and this solution was sprayed on the powdered mixture. The whole was dried in an oven, sifted and distributed into sachets, each containing 10 gm of aromatized granules.

Pluronic F 68 is the trade name of a condensation product of ethylene oxide and propylene glycol.

EXAMPLE 3

Complex granules in sachet units

|  | Grams |
|---|---|
| "Capillact" | 2 |
| Pyridoxal hydrochloride | 0.50 |
| Biotin | 0.002 |
| Citric acid | 0.10 |
| "Pluronic F 68" | 0.015 |
| Sodium cyclohexylsulfamate | 0.012 |
| Sodium saccharinate | 0.006 |
| Solid flavors } Liquid flavors } | 0.07 |
| Sugar powder, in a sufficient quantity to obtain a total weight of 10 gm. | |

The method of preparation of these granules was analogous to that described in Example 2.

EXAMPLE 4

Aromatized powder in 5 gm sachet units.

|  | Grams |
|---|---|
| "Capillact" | 1 |
| "Polvaromas Ananas" | 0.020 |
| "Polvaromas Vanilla" | 0.100 |
| "Avicel R.C." | 0.150 |
| Sugar powder | 3.730 |

The aromatized powder was prepared by mixing the above constituents and distributed in a sachet unit.

"Polvaromas Ananas" and "Polvaromas Vanilla" are trade names of aromatic fruit concentrates. "Avicel R.C." is the trade name of a microcrystalline cellulose.

EXAMPLE 5

Granules in combination with an antibiotic

|  | Grams |
|---|---|
| "Capillact" | 2 |
| Framycetin sulfate | 0.150 |
| Sodium saccharinate | 0.008 |
| Sodium cyclohexylsulfamate | 0.014 |
| "Pluronic F 68" | 0.090 |
| Citric acid | 0.100 |
| Solid flavors | 0.060 |
| Quinoline yellow | 0.003 |
| Sugar powder in a sufficient quantity to obtain a total weight of 5 gm. | |

The granules were prepared as in Example 2.

EXAMPLE 6

Granules in combination with an antiseptic

|  | Grams |
|---|---|
| "Capillact" | 2 |
| 5-chloro-7-iodo-8-oxyquinoline | 0.250 |
| Sodium saccharinate | 0.008 |
| Sodium cyclohexylsulfamate | 0.014 |
| "Pluronic F 68" | 0.090 |
| Citric acid | 0.100 |
| Solid flavors | 0.060 |
| Quinoline yellow | 0.003 |
| Sugar powder in a sufficient quantity for obtaining a total weight of 5 gm. | |

The granules were prepared as in Example 2.

PHARMACOLOGICAL STUDY

Test No. 1 Effect of Capillact on the tied intestinal loop of young rats subjected to an infection with a pathogenic colibacillus.

a. Preparation of culture broth

A culture of Escherichia Coli (E 65156, type $O_{26}B_6$) was developed in peptone broth (pH 8.4), and another culture was developed in a peptone broth containing 30 mgm/cc of Capillact. Both culture fluids were kept at 37° C for 24 hours. They were then innoculated with Escherichia Coli, type $O_{26}B_6$, obtained from culture on gelose with human blood, and kept for 5 hours.

b. Male rats weighing about 75 gm were fed with milk and water only from 24hours before the experiment to 24 hours after. After anesthesia with ethyl ether and laparotomy, an intestinal loop was tied over a length of 7 cm, and the ligatured loop of a lot of the animals was injected for control with 0.5 cc of the above-obtained culture of Escherichia Coli, while another part of the treatedanimals were injected with the Escherichia Coli culture containing 30 mgm/cc of "Capillact". All animals were sacrificed 24 hours after injection.

The increase in volume of the tied loop (V), the presence of liquid in the loop (L), and the inflammatory reaction (R) (hemorrhagic aspect) and the reaction of peritoneum were determined according to a subjective rating from 0 to 4+.

The results are summarized in Table I.

TABLE I

| | No. of the animal | Results | Reaction of peritoneum |
|---|---|---|---|
| Control | 1 | V +++<br>L +++<br>R ++ | ++ |
| | 2 | V ++<br>L ++<br>R +++ | + |
| | 3 | V ++++<br>L ++++<br>R ++ | +++ |
| | 4 | V ++<br>L ++<br>R ++++ | + |
| | 5 | V ++<br>L ++<br>R ++ | ++ |
| Treated | 6 | V +<br>L +<br>R O | 0 |
| | 7 | V +<br>L +<br>R + | 0 |
| | 8 | V ++++<br>L ++++<br>R +++ | + |
| | 9 | V O<br>L O<br>R O | 0 |
| | 10 | V ++<br>L ++<br>R O | 0 |

All the digestive viscera surrounding the tied loop were colored in red with inflammation in all control animals, while such inflammation was only noted in one animal among those treated with Capillact. There was no mortality in both groups of animals during the experiment.

Test No. 2 Effect against a typhic endotoxin.

The endotoxin used in this test consists of lipopoly saccharides extracted from *Salmonella typhosa* 0901 according to Westphal's method.

The procedure is identical with that of Test No. 1 above. The mixture of endotoxin and Capillact is kept for 1 hour at 22° C and then 12 hours at 4° C before injection.

The results are summarized in Table II.

TABLE II

| | No. of the animal | Results |
|---|---|---|
| Control (2.5 mg endotoxin alone) | 1 | V +++<br>L +++<br>R ++ |
| | 2 | V ++<br>L ++<br>R O |
| | 3 | V +<br>L +<br>R ++ |
| | 4 | V +<br>L +<br>R ++ |
| | 5 | V O<br>L O<br>R O |
| Treated (endotoxin 2.5 mg + 25 mg of "CAPILLACT") | 6 | V +<br>L +<br>R O |
| | 7 | V ++<br>L ++<br>R O |
| | 8 | V O<br>L O<br>R O |

Only one animal died 6 hours after injection.

Table II shows that Capillact displays a protection effect against typhic endotoxin. No inflammatory reaction of the surrounding viscera was observed.

Test No. 3 Effect of Capillact on tied intestinal loop of young rats subjected to infection with enterotoxic Staphilococci.

This test was conducted as Test No. 1 with a strain of enterotoxic Staphilococci E 58.

The results are summarized in Table III.

TABLE III

| | No. of the animal | Results | Peritoneum inflammatory reactions |
|---|---|---|---|
| Control innoculated with 0.5 cc of culture | 1 | V ++++<br>L ++++<br>R + | ++++ |
| | 2 | V ++++<br>L ++++<br>R ++ | ++++ |
| | 3 | V +++<br>L ++++<br>R ++ | ++++ |
| | 4 | V ++<br>L ++<br>R + | ++++ |
| Treated innoculated with 5 cc of culture containing 20 mg of "CAPILLACT" | 5 | V ++<br>L ++<br>R O | 0 |
| | 6 | V O<br>L O<br>R O | 0 |
| | 7 | V O<br>L O<br>R O | 0 |
| | 8 | V ++++<br>L ++++<br>R +++ | ++ |

All animals were alive in both groups 24 hours after the injection.

The results of Table III show that Capillact has a good effect against enterotoxic Staphilococci.

Test No. 4 Protective action against infection by enterotoxic Staphylocci on tied intestinal loop of young rats.

This test was conducted substantially as Test No. 1. Rats having an average weight of 80 gm were injected with 0.5 cc of a broth containing enterotoxic hemolytic *Staphylococcus aureus*, grown for 18 hours in Nutrient Broth Oxoid No. 2. Other animals received 15 mgm of Capillact in 0.5 cc of either an isotonic sodium chloride solution (study of tolerance) or 0.5 cc of a Staphylococcal broth (study of the protective action). Capillact was contacted for 3 hours with these solutions before use.

The results are summarized in Table IV.

TABLE IV

| Treatment | No. of the animal | Results | Peritoneal reactions | Number of animals alive after 24 hours |
|---|---|---|---|---|
| | 1 | V +++<br>L +++<br>R + | 0 | |
| "Capillact" 15 mgm + 0.5 cc of isotonic solution of sodium chloride | 2 | V O<br>L O<br>R O | O | 3/3 |
| | 3 | V ++<br>L ++<br>R + | O | |
| | 4 | V ++++<br>L ++++<br>R ++++ | +++ | |
| Control- 0.5 cc of Staphyloccic broth | 5 | V ++++<br>L ++++<br>R ++++ | +++ | 4/4 |
| | 6 | V +++<br>L +++<br>R + | +++ | |
| | 7 | V +++<br>L +++<br>R + | ++ | |
| | 8 | V ++<br>L ++<br>R +++ | 0 | |
| | 9 | V ++<br>L ++<br>R + | 0 | |
| Treated 15 mgm of "Capillact" + 0.5 cc of Staphyloccal broth | 10 | V +<br>L +<br>R + | 0 | 3/5 |
| | 11 | V +<br>L +<br>R + | 0 | |
| | 12 | V +<br>L +<br>R O | 0 | |

Table IV shows that Capillact strongly lessens the local inflammatory reactions caused by Staphylococci.

Test No. 5 Activity against Candida albicans injected in a tied intestinal loop of young rats.

The strain of Candida albicans was obtained by puncture of a gallbladder.

Capillact was contacted for 6 hours with the Candida albicans broth before use.

The procedure is the same as that of Test No. 1
The results are summarized in Table V.

TABLE V

| Treatment | No. of the animal | Results | Peritoneal inflammatory reaction |
|---|---|---|---|
| | 1 | V ++++<br>L ++++<br>R ++++ | ++ |

TABLE V-continued

| Treatment | No. of the animal | Results | Peritoneal inflammatory reaction |
|---|---|---|---|
| | 2 | V ++++<br>L ++++<br>R ++++ | ++ |
| | 3 | V +++<br>L +++<br>R +++ | ++ |
| Control (0.5 cm3 of broth) | 4 | V ++++<br>L ++++<br>R +++ | + |
| | 5 | V ++<br>L ++<br>R + | + |
| | 6 | V ++++<br>L ++++<br>R ++++ | ++ |
| | 7 | V ++++<br>L ++++<br>R ++ | ++ |
| | 8 | V ++++<br>L ++++<br>R +++ | 0 |
| | 9 | V ++<br>L ++<br>R + | 0 |
| | 10 | V ++++<br>L ++++<br>R + | 0 |
| Treated (0.5 mgm of broth + 20 mgm of "Capillact") | 11 | V ++++<br>L ++++<br>R ++ | 0 |
| | 12 | V ++++<br>L ++++<br>R + | 0 |
| | 13 | V +++<br>L +++<br>R O | 0 |
| | 14 | V +<br>L +<br>R + | 0 |

All animals were alive after 24 hours. No peritoneal inflammatory reaction was noted in animals treated with 20 mgm of Capillact, and the inflammatory reaction of the tied loop was noticeably reduced in these treated animals.

Test No. 6 Tolerance of the intestinal loop of young rat to Capillact.

The procedure is analogous to that of Test No. 1, except that the intestinal loops were injected only with various doses of "Capillact" prepared in 0.5 cc of water at least 1 hour before the experiment.

The results are summarized in Table VI.

TABLE VI

| Treatment | No. of the animal | Results |
|---|---|---|
| | 1 | V O<br>L O<br>R O |
| 10 mgm of "Capillact" in 0.5 cc of distilled water | 2 | V O<br>L O<br>R O |
| | 3 | V ++<br>L ++<br>R O |
| | 4 | V +++<br>L +++<br>R O |
| | 5 | V O<br>L O<br>R O |
| 20 mgm of "Capillact" in 0.5 cc of distilled water | 6 | V +++<br>L +++<br>R O |
| | 7 | V +<br>L +<br>R + |

TABLE VI-continued

| Treatment | No. of the animal | Results |
|---|---|---|
| | 8 | V O<br>L O<br>R O |
| | 9 | V O<br>L O<br>R O |
| 30 mgm of "Capillact"<br>in 0.5 cc of dis-<br>tilled water | 10 | V ++<br>L ++<br>R + |
| | 11 | V O<br>L O<br>R + |
| | 12 | V O<br>L O<br>R O |

With 10 mgm of Capillact, no hemorrhagic-like inflammatory reaction was observed.

With 20 mgm of Capillact, a slight inflammatory reaction was noted in 1 case.

With 30 mgm of Capillact, which is a very large dose under the conditions of this experiment, a slight inflammatory reaction was noted in 2 cases.

In another experiment rats weighing 60 to 70 gm were distributed into 2 groups. Group 1 received 15 mgm Capillact contacted for 6 hours with 0.5 cc of an isotonic sodium chloride solution. Group 2 received 20 mgm of Capillact contacted for 6 hours with 0.5 cc of the isotonic solution. The procedure is the same as above. The results are summarized in Table VII.

TABLE VII

| Groups | No. of animal | Results |
|---|---|---|
| Group 1 | 1 | V O<br>L O<br>R O |
| | 2 | V O<br>L O<br>R O |
| | 3 | V O<br>L O<br>R O |
| | 4 | V O<br>L O<br>R O |
| | 5. | V O<br>L O<br>R O |
| Group 2 | 6 | V ++++<br>L ++++<br>R O |
| | 7 | V +++<br>L +++<br>R O |
| | 8 | V O<br>L O<br>R O |
| | 9 | V ++<br>L ++<br>R O |
| | 10 | V O<br>L O<br>R O |

All animals were alive after 24 hours. Inflammatory reactions were substantially absent, except in one case where a slight reaction was noted.

Test No. 7 Effects on intoxication with *Escherichia Coli* endotoxin.

Lipopoly saccharides obtained from *Escherichia coli* $O_{127}B_8$ by extraction with phenol according to Westphal's method were used as endotoxin. The *Escherichia Coli* was obtained from patients suffering of infantile gastroenteritis.

The endotoxin was suspended in physiologic serum and the endotoxin-Capillact mixture was kept for 4 hours before use. A group of mice of average weight 20 gm were injected with 0.8 cc of this mixture (treated animals). For control, another group of animals received the same volume of a serum suspension of endotoxin alone. The mortality of the animals was observed. The results are summarized in Table VIII. Each group was composed of 10 amimals.

TABLE VIII

| Animals | Mortality at various time intervals (in hours) after injection. | | | | | | Number of animals alive after 7 days |
|---|---|---|---|---|---|---|---|
| | 16 H | 18 H | 20 H | 23 H | 40 H | 60 H | |
| Control (1.25 mgm endotoxin alone) | 3 | 2 | 1 | 1 | 1 | 1 | 1 |
| Treated (endotoxin 1.25 mgm + "Capillact") | | 1 | 1 | 3 | | | 5 |

From these results, it can be concluded that Capillact has an important power of adsorption of *Escherichia Coli* endotoxins.

Test No. 8 Adsorption of endotoxin from *Escherichia Coli* by Capillact.

Lipopolysaccharide endotoxin of *Escherichia Coli* $O_{111}B_4$ is extracted according to Westphal's method. The mice were injected intraperitoneally either with 1 cc of endotoxin in 1 cc of a buffered physiologic serum (pH 6.5) or with 1 cc of endotoxin containing 200 mgm of Capillact. The mixture of endotoxin and Capillact was kept for 6 hours at 22° C before use.

The mortality of animals in both groups is summarized in Table IX.

TABLE IX

| | Mortality after | | | | Number of animals alive after 7 days |
|---|---|---|---|---|---|
| | 15 Hours | 18 Hours | 60 Hours | 84 Hours | |
| Control | 4 | 1 | 2 | 1 | 2/10 |
| Treated | 1 | 2 | 1 | | 6/10 |

Table IX shows that Capillact is noticeably effective against *Escherichia Coli* endotoxin.

Test No. 9 Adsorption of *Salmonella enteritidis* endotoxin

Endotoxin, consisting of lipopolysaccharides extracted from *Salmonella enteritidis*, was used in this experiment (Ref. Difco No. 3105).

Mice weighing from 32 to 35 gm were divided into 4 groups of 10 animals each.

The animals were intraperitoneally injected with the following compositions:

Group 1 — 1 mgm of endotoxin suspended in 1 cc of Difco buffered solution, pH = 7.2 - 7.3.

Group 2 — 2 mgm of endotoxin suspended in 1 cc of the same buffered solution

Group 3 — 1 cc of residual liquid obtained from 1 mgm of endotoxin suspended in Difco buffered solution and 200 mg of Capillact after 3 hours of contact.

Group 4 — 1 cc of residual liquid obtained from 2 mgm of endotoxin and 200 mgm of Capillact after 3 hours of contact.

The mortality of the animals at various time intervals, expressed in hours, and after the seventh day, is summarized in Table X.

TABLE X

|  | Mortality after | | | | |
| --- | --- | --- | --- | --- | --- |
|  | 16 Hours | 24 Hours | 40 Hours | 62 Hours | Number of animals alive after 7 days |
| Group 1 | 2 | 2 | 3 |  | 3 |
| Group 2 | 2 | 6 | 1 |  | 1 |
| Group 3 |  |  |  |  | 10 |
| Group 4 |  |  | 1 |  | 9 |

Table X shows that 200 mgm of Capillact can adsorb more than 1 mgm of the endotoxin extracted from *Salmonella enteritidis*.

Test No. 10 Adsorption by *Escherichia Coli* endotoxin by Capillact.

The endotoxin used in this test consists of polylipo-saccharides extracted from *Escherichia Coli*, strain $O_{26}B_6$ by Boivin's method (Difco 3920 - 25).

Two groups of 10 mice weighing 20 gm each were utilized:

Group 1 — received intraperitoneally 1.5 mgm of endotoxin suspended in 1 cc of buffered Difco solution.

Group 2 — received the residual liquid obtained from 1.5 mgm of endotoxin suspended in buffered Difco solution and 200 mg of Capillact after 3 hours of contact.

The results are summarized in Table XI.

TABLE XI

|  | Mortality after | | | |
| --- | --- | --- | --- | --- |
|  | 16 Hours | 20 Hours | 24 Hours | Number of animals alive after 7 days |
| Group 1 | 5 | 3 | 1 | 1 |
| Group 2 | 1 | 2 | 2 | 5 |

The results of Table XI corroborate the results of the preceding tests showing that Capillact has an interesting adsorption power of various microbial toxins.

Test No. 11 Adsorption of *Serrati marcescens* endotoxin

The endotoxin used in this test was extracted from *Serrati marcescens* (code 3881 Difco) by the method with trypsin.

The procedure is analogous to that of Test No. 10. Group 1 received 2 mg of endotoxin suspended in 1 cc of buffered Difco solution. Group 2 received 1 cc of residual liquid obtained from 2 mgm of endotoxin suspended in buffered Difco solution and 200 mg of Capillact after 3 hours of contact.

The results are summarized in Table XII.

TABLE XII

|  | Mortality after | | |
| --- | --- | --- | --- |
|  | 16 Hours | 24 Hours | Number of animals alive after 7 days |
| Group 1 | 3 | 1 | 6/10 |
| Group 2 |  |  | 10/10 |

Table XII shows that an important amount of the endotoxin was absorbed by Capillact.

Test No. 12 Adsorption of *Salmonella typhosa* endotoxin by Capillact.

The endotoxin consisted of lipopolysaccharides obtained from *Salmonella typhosa* /Ref. (Difco 0901) by Westphal's method.

Mice weighing 20–22 gm were distributed into 7 groups which were treated as summarized in Table XIII.

The procedure was identical with that of Test No. 9. The results are summarized in Table XIII.

TABLE XIII

|  | Mortality after | | | | | Number of animals alive after 6 days. |
| --- | --- | --- | --- | --- | --- | --- |
|  | 15 Hours | 18 Hours | 21 Hours | 40 Hours | 90 Hours | |
| Group 1 (control) 0.5 mgm of endotoxin | 1 |  |  | 1 |  | 8/10 |
| Group 2 (control) 1 mgm of endotoxin | 3 |  | 2 | 2 | 1 | 2/10 |
| Group 3 (control) 2 mgm of endotoxin | 6 | 2 | 1 |  |  | 1/10 |
| Group 4: 0.5 mgm of endotoxin + 100 mgm of "Capillact" |  |  |  | 1 |  | 9/10 |
| Group 5: 0.5 mgm of endotoxin + 200 mgm of "Capillact" |  |  |  |  |  | 10/10 |
| Group 6: 1 mgm of endotoxin + 200 mgm of "Capillact" | 1 |  |  | 2 |  | 7/10 |
| Group 7: 2 mgm of endotoxin + 200 mgm | 4 |  |  | 2 |  | 4/10 |

TABLE XIII-continued

|  | Mortality after | | | | | Number of animals alive after 6 days. |
|---|---|---|---|---|---|---|
|  | 15 Hours | 18 Hours | 21 Hours | 40 Hours | 90 Hours | |
| of "Capillact" | | | | | | |

These results show the important activity of Capillact against Salmonella typhosa endotoxin.

Test No. 13 Activity of Capillact against high doses of endotoxins.

The endotoxin consisted of lipopolysaccharides obtained from *Salmonella enteridis* (Ref. Difco 3126) by Westphal's method. The 3 mg of endotoxin suspended in 1 cc of water was intraperitoneally injected in mice weighing 20-22 gm, with or without Capillact.

The results are summarized in Table XIV.

TABLE XIV

|  | Mortality After | | | | | Number of animals alive after 7 days |
|---|---|---|---|---|---|---|
|  | 16 Hours | 17 Hours | 20 Hours | 22 Hours | 24 Hours | 40 Hours | |
| Control: 3 mgm of endotoxin | 6 | 1 | 2 | | | | 1/10 |
| Treated: 3 mgm of endotoxin + 200 mgm of "Capillact" | | | | 3 | 2 | 2 | 3/10 |

In another series of experiments, the animals were injected with lipopolysaccharides obtained from *Schigella Flexneri* (Ref. Difco 3107) by Boivin's method under the same conditions as above. The results are summarized in Table XV.

TABLE XV

|  | Mortality after | | | Number of animals alive after 7 days. |
|---|---|---|---|---|
|  | 24 Hours | 46 Hours | 72 Hours | |
| Control: 3 mgm of endotoxin | 8 | 2 | | 0/10 |
| Treated: 3 mgm of endotoxin + 200 mgm of "Capillact" | 1 | | 1 | 8/10 |

These two experiments, and particularly the second one, show the very clear detoxicant activity of Capillact.

CLINICAL TESTS

The product was administered in the form of 1 or 2 sachet-units, each containing 2 gm of Capillact per day in common diarrhea consecutive to food poisoning as well as in critical diarrhea occuring in crisis of chronic colitis.

The clinical reports are summarized in Table XVI.

TABLE XVI

| Patient | Diagnosis | Dosage | Results | Tolerance |
|---|---|---|---|---|
| 1 | Common diarrhea for 4 days; 5 to 6 liquid stools a day. | 1 sachet per day | Very good. Disappearance of diarrhea in 36 hours. Normal stools on second day. | Good |
| 2 | Diarrhea for 5 days due to food poisoning. Abdominal pains. | 1/2 sachet twice a day | Improvement in 24 hours. Normal stools after 2 days. Disappearance of pain. | Good |
| 3 | Chronic colitis in a beer drinker. Diarrhea for 8 days after excess in alimentation. | 2 sachets per day. | Good results. Regularization of intestinal transit in 2 days. | Good |
| 4 | Transverse colitis. 4 to 5 diarrhaic stools a day for 4 days. Failure of a treatment with bismuth and charcoal. | 2 sachets per day. | Very good results, despite a remaining slight aerocolia. | Good |
| 5 | Food poisoning. Liquid stools. Abdominal pain. | 1 sachet per day. | Fast improvement. Normal intestinal transit in 48 hours. | Good |
| 6 | Bipolar colitis in an ex-amoebic patient. | 2 sachets a day. | Average | Good |
| 7 | Diet excess in a colitic patient resulting in critical diarrhea. Usual therapeutics without effect. | 1 sachet a day. | Good. Normal intestinal transit in 48 hours. | Good |

TABLE XVI-continued

| Patient | Diagnosis | Dosage | Results | Tolerance |
|---|---|---|---|---|
| 8 | Colitis in a dysenteric patient. Painful spasms of left colon. | 2 sachets a day. | Good. Normal transit after a few days. Disappearance of pain. | Good |
| 9 | Diarrhea for 3 days with some fever after a diet excess. Insufficient results with charcoal and bismuth. | 2 sachets a day. | Very good. Normal stools after 2 days. | Good |
| 10 | Food poisoning. Diarrhea; numerous liquid stools. Abdominal pain. | 1 sachet a day. | Good results. Fast disappearance of pain. Regularization of transit. | Good |
| 11 | Critical diarrhea in a biliary dyskinetic patient after a diet excess. | 1 sachet a day. | Very good. | Good |
| 12 | Persistent diarrhea after treatment with tetracycline, despite prophylactic administration of yeast. | 2 sachets a day. | Progressive improvement, then regularization of intestinal transit after 5 days. | Good |
| 13 | Spastic colitis, critical diarrhea. Painful spasms of left colon. | 2 sachets a day. | Good results on both diarrhea and pain in 3 days. | Good |
| 14 | Diarrhea (probably fermentative) in a chronic colitic patient for a fortnight with starchy food excess habits. | 2 sachets a day. | progressive improvement. Regularization in 5 days. | Good |
| 15 | Benign food poisoning (iced drinks, diet excess) | 1 sachet a day. | Complete recovery in 36 hours. | Good |

Various modifications of the compositions and methods of the invention may be made without departing from the spirit and scope thereof.

We claim:

1. A method of treating chronic or infectious diarrhea in humans and warm-blooded animals suffering from symptoms or diarrhea caused by infections, food poisonings, changes in diet, excessive use of laxatives, diseases of extra-intestinal origin, and treatment with antibiotics, which consist essentially of orally administering an effective antidiarrheal amount of from 25 to 125 mg/kg daily of a formaldehyde-modified casein consisting of rennet casein reacted with from 0.6 to 2.5 gm per 100 gm of formaldehyde in the presence of an aqueous medium, and freed of unreacted formaldehyde.

2. The method of claim 1 wherein said formaldehyde-modified casein is orally administered in the form of powder granules distributed in sachet units.

* * * * *